United States Patent [19]

Wetzel et al.

[11] Patent Number: 5,721,280
[45] Date of Patent: Feb. 24, 1998

[54] METHOD FOR DEPOLYMERIZING POLYIMIDES AND RECOVERING REAGENTS THEREFROM

[75] Inventors: Joseph Richard Wetzel, Watervliet; Andrew James Caruso, Schenectady, both of N.Y.

[73] Assignee: General Electric Company, Schenectady, N.Y.

[21] Appl. No.: 726,962

[22] Filed: Oct. 7, 1996

[51] Int. Cl.$^6$ .................................... C08J 11/08
[52] U.S. Cl. .................... 521/49; 521/49.5; 526/262; 528/488; 528/492; 528/503
[58] Field of Search ............... 521/49, 49.5; 526/262; 528/488, 492, 503

[56] References Cited

U.S. PATENT DOCUMENTS 3,529,017  9/1970  Izard et al. ............................... 562/483
4,349,479  9/1982  Takekoshi et al. ..................... 548/461
4,451,643  5/1984  Edmonds, Jr. et al. ................ 528/387

*Primary Examiner*—Vasu Jagannathan
*Assistant Examiner*—Olga Asinovsky
*Attorney, Agent, or Firm*—William H. Pittman

[57] ABSTRACT

Polyimides, especially thermoset polyimides such as those prepared by the reaction of p-phenylenediamine with 4,4'-hexafluoroisopropylidenebis(phthalic anhydride) and nadic ester, are converted to monomers which may be recycled for polyimide synthesis by heating with a solution of an alkali metal hydroxide, such as lithium hydroxide or sodium hydroxide, in a dipolar aprotic solvent such as N-methylpyrrolidone. The products are the diamine and the tetracarboxylic acid alkali metal salt corresponding to the dianhydride.

16 Claims, No Drawings

METHOD FOR DEPOLYMERIZING POLYIMIDES AND RECOVERING REAGENTS THEREFROM

This invention was made with Government support under contract number F49620-94-C0026 awarded by the Department of the Air Force. The Government has certain rights in this invention.

BACKGROUND OF THE INVENTION

This invention relates to the recovery of organic values from polyimides, and more particularly to the recycle of useful polyimide-forming chemicals.

Polyimides are a class of engineering polymers in wide use by reason of their excellent properties, including resistance to solvents and to high temperatures. They are commonly prepared by the reaction of tetracarboxylic acid dianhydrides with diamines. Also present in many instances are fillers, illustrated by fibrous materials including glass fibers and carbon fibers.

Many of the polyimide-forming chemicals, particularly the dianhydrides, are very expensive. A singular example is 4,4'-hexafluoroisopropylidenebis(phthalic anhydride) (hereinafter "6FDA"), which costs substantially more than $500/kg. Thus, such polyimides are in wide use only in high technology electronic applications and the like, where cost of raw materials is only a minor factor.

An illustrative polyimide whose extent of use is impaired by its high cost is the thermoset polyimide designated as AFR-700B. It is prepared by the reaction of 6FDA or the corresponding tetracarboxylic acid or diester thereof with p-phenylenediamine and bicyclo[2.2.1]heptane-2,3-dicarboxylic acid or a partial ester thereof (such as the monomethyl ester, commonly known as "nadic ester") to form an amine- and nadic ester-terminated prepolymer. The next step is thought to involve a retro Diels-Alder reaction with the liberation of cyclopentadiene and the formation of a maleimide terminal group which is an efficient crosslinking site.

Most often, a fibrous reinforcement is impregnated with the monomers in solution. The solvent is removed and the monomer-fiber matrix is heated to form an oligomer, which then undergoes curing to form a crosslinked, thermoset composite having exceptional thermal stability.

Since the crosslinking reaction is not believed to involve the 6FDA or diamine moieties in the polyimide, it is possible to visualize a recycle method by which scrap polymer could be reconverted to 6FDA, p-phenylenediamine and fibers. Any or all of these could then be recovered and recycled. Most advantageous would be recycle of 6FDA, since it is such a high cost material. Recycle of p-phenylenediamine would also be advantageous; at the very least, it should be totally recovered for careful destruction and/or disposal, since it presents environmental hazards.

Various recycle methods for polyimides, particularly thermoplastic polyimides, are known in the art. They include aminolysis as described in U.S. Pat. No. 4,349,479 and alkaline hydrolysis as described, for example, in Soviet Union patent application 76/2,354,720; Chemical Abstracts, 114, 124,260b (1993); and U.S. Pat. No. 3,529,017. However, even as applied to thermoplastic polymers these methods suffer from deficiencies which have inhibited their wide use. In the first place, alkaline hydrolysis procedures can result in attack on reinforcing materials such as glass fibers, resulting in significant degradation thereof. In the second place, an important use of these polyimides is in electronics applications where very low metal levels, as illustrated by a maximum sodium level of 15 ppm or lower, are required and it is difficult to attain such levels after an alkaline hydrolysis operation.

In any event, the above-described recycle methods are generally not applicable to thermoset polyimides, at least in part by reason of their chemical complexity and the difficulty in recovering quality monomers from the complex mixtures obtained. Thus, there are presently no known recycle methods of convenience applicable to thermosets.

Thus, the need remains for a convenient and effective method for recycle of polyimides, with conversion to useful polyimide-forming chemical intermediates.

SUMMARY OF THE INVENTION

The present invention is a method for recycling a polyimide which comprises heating said polyimide with a solution of an alkali metal hydroxide in a dipolar aprotic solvent for a time and at a temperature and pressure effective to convert said polyimide to at least one tetracarboxylic acid or functional derivative thereof and at least one diamine or functional derivative thereof.

DETAILED DESCRIPTION; PREFERRED EMBODIMENTS

Any polyimide can be recycled by the method of this invention. Illustrative polyimides are those prepared from such dianhydrides as pyromellitic dianhydride, 2,2-bis[4-(3,4-dicarboxyphenoxy)phenyl]propane dianhydride (hereinafter "BPADA"), 3,3',4,4'-benzophenonetetracarboxylic dianhydride, 3,3',4,4'-biphenyltetracarboxylic dianhydride, 3,4-dicarboxyphenyl ether dianhydride and 6FDA, and such diamines as m-phenylenediamine, p-phenylenediamine and 4-aminophenyl ether. The invention is particularly useful for recycle of the polyimides prepared from 6FDA and p-phenylenediamine, and especially the fiber-reinforced polyimides. In a still more preferred embodiment, the invention is utilized with thermoset polyimides as illustrated by AFR-700B.

The essential recycle reagents are an alkali metal hydroxide and a dipolar aprotic solvent. Suitable alkali metal hydroxides include lithium hydroxide, sodium hydroxide and potassium hydroxide. Lithium hydroxide and sodium hydroxide are frequently preferred by reason of their relatively low cost, favorable solubility in dipolar aprotic solvents and relative inertness to glass fibers under the prevailing reaction conditions.

The dipolar aprotic solvents which may be employed include principally those having a boiling point at atmospheric pressure of at least about 150° C., preferably at least about 175° C. Illustrative solvents of this type are dimethylformamide, dimethylacetamide, dimethyl sulfoxide and N-methylpyrrolidone (1-methyl-2-pyrrolidone, hereinafter sometimes "NMP"). NMP is often preferred by reason of its particular effectiveness. It is not necessary for the dipolar aprotic solvent to be anhydrous. However, it is usually convenient to employ an anhydrous solvent or one which contains, at most, about 1% by weight of water based on solvent.

In the method of the invention, the polyimide or composite comprising the same is typically first cut into conveniently handled pieces, which are placed in a suitable reactor with the alkali metal hydroxide and aprotic solvent. Suitable reactors include those which can operate at atmospheric pressure and also those useful at higher pressures, typically up to about 3 atmospheres and preferably up to about 7 atmospheres.

Temperatures on the order of 180°–250° C. are usually employed. The reaction may be conducted under autogenous pressure, generally up to about 3 atm. In general, the combination of temperatures above about 275° C. and pressures above about 6.5 atm should be avoided since under these relatively severe conditions, various by-products may be formed in substantial quantities.

The proportion of alkali metal hydroxide employed should be a relatively large excess, typically a molar ratio to tetracarboxylic acid moieties in the polyimide of at least about 8:1 and preferably at least 10:1. Solvent proportions are not critical but are typically such as to provide an alkali metal hydroxide concentration on the order of 1–2 moles/l.

The product obtained by reaction of the alkali metal hydroxide with the polyimide comprises the polyimide reinforcing agent(s) if any, a functional derivative which is usually the alkali metal salt of the tetracarboxylic acid from which the polyimide is derived, and the amine from which the polyimide is derived. Reinforcing agent, especially fibrous filler, may be isolated by washing with organic solvent and water, filtering and drying. When so isolated, it is frequently suitable for recycle to prepare further reinforced polyimide. The amine may be recovered by dissolution in a suitable organic solvent such as ethyl ether and/or ethyl acetate to form a solution which may be washed with water, acidified and stripped for recovery of the amine.

For recovery of the tetracarboxylic acid, the alkali metal salt may be acidified and extracted with an organic solvent. The organic extracts contain the acid which may be isolated by conventional means and converted if desired to a functional derivative such as the dianhydride.

The method of this invention is illustrated by the following examples.

EXAMPLE 1

A 2-l stainless steel pressure reactor was charged with 59.5 g of cured, scrap avionic composite containing AFR-700B polyimide in the form of large strips. The polyimide had a degree of polymerization of 8 and contained 550 mmol of 6FDA units per gram of composite, as determined by combustion analysis of fluorine. There were added 31 g (1.29 moles) of lithium hydroxide and 1 l of anhydrous NMP. The reactor was purged with nitrogen and heated for 5 hours at 250° C., under autogenous pressure of about 6.8 atm. It was then allowed to cool overnight.

Large strips of woven fiber were removed manually from the reaction mixture, washed with a small amount of NMP and then with 1 l of water, filtered and vacuum dried. There was recovered 40.95 g of white strands of fiber, shown upon analysis to contain 0.054% carbon. From this value and the original carbon value for the reinforced polyimide of 18.12%, it was calculated that the depolymerization was 99.8% effective. The lithium content of the recovered fiber was less than 83 ppm.

The dark liquid mixture remaining in the reaction vessel was evaporated to dryness in vacuum; the stripped liquid was NMP recovered in near-quantitative yield. There remained a dark solid which was washed with four 100-ml portions of ethyl ether to form a first wash liquid. The first wash liquid was set aside and the remaining solid was dissolved in a minimal amount of water, after which the resulting aqueous solution was washed with 200 ml of ethyl acetate to form a second wash liquid.

The first and second wash liquids were combined, dried over magnesium sulfate, filtered and concentrated to one-third of their original volume. An excess of hydrochloric acid in solution in ethyl acetate was added, whereupon a pink solid deposited. It was removed by filtration, washed with anhydrous ethyl ether and vacuum dried to yield p-phenylenediamine dihydrochloride in a total yield of about 55% of theoretical.

The aqueous solution, after washing with ethyl acetate, was cooled in ice and 200 ml of ethyl acetate was added. The mixture was acidified with concentrated hydrochloric acid to a pH of 3 and extracted with four 100-ml portions of ethyl acetate. The extracts were combined and reextracted with three 100-ml portions of 10% aqueous sodium bicarbonate solution. The aqueous extracts were combined and cooled in ice, 200 ml of ethyl acetate was added and the mixture was again acidified with concentrated hydrochloric acid and extracted with four 100-ml portions of ethyl acetate. The combined organic extracts were washed with aqueous sodium chloride solution, dried over magnesium sulfate, filtered and concentrated to yield 11.2 g of the desired 4,4'-hexafluoroisopropylidenebis(phthalic acid) as a light tan foam. Its structure was confirmed by proton nuclear magnetic resonance spectroscopy.

EXAMPLE 2

An 11-g sample of the crude tetracarboxylic acid from Example 1 was heated in a vacuum sublimation apparatus at 240°–280° C./0.01–0.05 torr for 1 hour. The light yellow solid which condensed on the cold finger in the apparatus was extracted with ethyl acetate and the extract was dried over magnesium sulfate, filtered and vacuum stripped to yield a light yellow solid which was filtered, washed with cold ethyl ether and dried under vacuum. It was shown by proton and carbon-13 nuclear magnetic resonance spectroscopy to be the desired 6FDA, obtained in a yield of about 58% of theoretical based on fluorine combustion analysis of the starting composite. It was shown upon analysis to have a lithium/sodium content of less than 16 ppm, the detection limit of the analytical method.

EXAMPLE 3

The procedure of Example 1 is repeated, substituting sodium hydroxide on an equimolar basis for the lithium hydroxide. The same products are obtained in similar yields.

EXAMPLE 4

The procedure of Example 1 was repeated, except that the reaction was run at 225° C. and an autogenous pressure of about 2.7 atm. Similar results were obtained after a reaction time in the range of 2–5 hours.

EXAMPLE 5

The procedure of Example 1 was repeated, except that the reaction was run at the boiling point of NMP (about 190° C.) and atmospheric pressure. Similar results were obtained after a reaction time of about 15 hours.

What is claimed is:

1. A method for recycling a -fiber-reinforced- polyimide which comprises heating said polyimide with a solution of an alkali metal hydroxide in a dipolar aprotic solvent wherein the solvent is dimethylformamide, dimethylacetamide, dimethyl sulfoxide or N-methylpyrrolidone for a time and at a temperature and pressure effective to convert said polyimide to at least one tetracarboxylic acid or functional derivative thereof and at least one diamine or functional derivative thereof.

2. A method according to claim 1 wherein the polyimide is a thermoset polyimide.

3. A method according to claim 2 wherein the alkali metal hydroxide is lithium hydroxide or sodium hydroxide.

4. A method according to claim 2 wherein the tetracarboxylic acid is pyromellitic acid, 2,2-bis[4-(3,4-dicarboxyphenoxy)phenyl]propane or 4,4'-hexafluoroisopropylidenebis(phthalic acid).

5. A method according to claim 4 wherein the tetracarboxylic acid is 4,4'-hexafluoroisopropylidenebis(phthalic acid).

6. A method according to claim 5 further comprising the step of recovering said 4,4'-hexafluoroisopropylidenebis (phthalic acid) for use in polyimide synthesis.

7. A method according to claim 2 wherein the diamine is m-phenylenediamine, p-phenylenediamine or 4-aminophenyl ether.

8. A method according to claim 7 wherein the diamine is p-phenylenediamine.

9. A method according to claim 8 further comprising the step of recovering said p-phenylenediamine for use in polyimide synthesis.

10. A method according to claim 2 wherein the temperature is in the range of about 180°–250° C.

11. A method according to claim 10 wherein the pressure is autogenous pressure.

12. A method according to claim 2 wherein the molar ratio of alkali metal hydroxide to tetracarboxylic acid moieties in the polyimide is at least about 8:1.

13. A method according to claim 12 wherein the proportion of solvent is such as to provide an alkali metal hydroxide concentration of about 1–2 moles/l.

14. A method according to claim 2 wherein the reinforcing agent therein is also isolated.

15. A method according to claim 14 wherein the fibers are glass fibers.

16. A method according to claim 14, wherein the fibers are carbon fibers.

\* \* \* \* \*